United States Patent [19]

Schwartz

[11] 4,153,509

[45] May 8, 1979

[54] MICROBIAL PRODUCTION OF HYDROXYLATED BIPHENYL COMPOUNDS

[75] Inventor: Robert D. Schwartz, Nitro, W. Va.

[73] Assignee: Union Carbide Corporation, New York, N.Y.

[21] Appl. No.: 842,808

[22] Filed: Oct. 17, 1977

[51] Int. Cl.² ............................................. C07B 29/02
[52] U.S. Cl. .................................................. 195/51 R
[58] Field of Search ............................ 195/51 R, 28 R

[56] References Cited

U.S. PATENT DOCUMENTS

| 3,352,884 | 11/1967 | Fonken et al. | 195/51 R |
| 3,755,080 | 8/1973 | Wegner | 195/28 R |

OTHER PUBLICATIONS

Smith et al., Arch. Biochem. Biophys. 161, pp. 551–558 (1974).
Ohmori et al., Agr. Biol. Chem. 37, pp. 1599–1605 (1973).
Gibson et al., Biochem. Biophys. Res. Commun. 50, pp. 211–219 (1973).
Catelani et al., Biochem. J. 134, pp. 1063–1066 (1973).
Catelani et al., Biochem. J. 143, 431–434 (1974).
Wiseman et al., Biochem. Soc. Trans. 3, pp. 278–281 (1975).

*Primary Examiner*—Alvin E. Tanenholtz
*Attorney, Agent, or Firm*—Robert C. Brown

[57] ABSTRACT

A process for preparing hydroxylated biphenyl compounds by enzymatically biotransforming the biphenyl compound with a microorganism.

13 Claims, No Drawings

MICROBIAL PRODUCTION OF HYDROXYLATED BIPHENYL COMPOUNDS

SUMMARY OF THE INVENTION

This invention relates to a process for preparing di- or mono- hydroxy derivatives of biphenyl compounds.

More particularly, this invention relates to a process for producing mono and di hydroxy biphenyl compounds by emzymatically biotransforming the corresponding biphenyl compound with a microorganism.

DESCRIPTION OF THE PREFERRED EMBODIMENTS

The biphenyl compounds that can be employed as reactants in the process of this invention include biphenyl compounds in which the phenyl moieties may be connected by a divalent hydrocarbon radical which may optionally include one or more oxygen, nitrogen, sulfur sulfinyl, sulfonyl in any combination. The carbon atoms can be acyclic or cyclic; saturated and/or unsaturated such as aliphatic, cycloaliphatic or bicycloaliphatic including fused and bridged carbon atoms and the like. The nitrogen component may be in the form of imino, amino, aliphatic amino or the like. The oxygen containing components can be groups such as hydroxyl, carbonyloxy, carbonyl, ether groups and the like. The sulfur component may be sulfur in any of its oxidation states, such as sulfur, sulfinyl or sulfonyl groups. The biphenyl compound inclusive of the bridging hydrocarbon radical may be substituted with one or more substituents such as chlorine, alkyl, alkoxy, fluorine, bromine, nitro, hydroxyl, iodine and the like, the only requirement being that the substituent be unreactive to the microorganism, unless multiple reactions are desired.

Preferred biphenyl reactants are those of the formula:

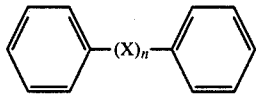

n is 0 or 1 or 2;
X is phenyl, divalent oxygen, sulfur, sulfinyl, sulfonyl, carbonyl, amino or alkylamino or X is a divalent alkylene, alkenylene or alkynylene chain which may optionally include one or more divalent oxygen, sulfur, sulfinyl, sulfonyl, carbonyl, amino or alkylamino moieties in any combination.

Illustrative of suitable biphenyl reactants are:
Biphenyl,
4-Hydroxybiphenyl
Biphenylmethane
Biphenylethane
Biphenylpropane
Benzophenone
Benzil
Diphenylacetylene
Diphenylsulfide
Diphenylsulfone
Diphenylether
p-Terphenyl
Biphenylethylene The biphenyl compounds useful as reactants in the process of invention are known compounds that can be obtained from commercial sources or prepared in accordance with well known synthetic procedures.

Illustrative of hydroxy biphenyl derivatives that can be prepared by the process of this invention are those of the formula:

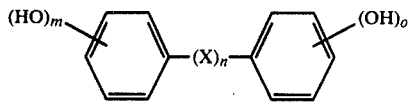

wherein:
m and O are individually 1 or 0 with the proviso that both m and O may not be 0.
X and n are as described above.

The process of this invention is particularly useful for preparing hydroxyated biphenyl derivatives with hydroxyl groups substituted at one or both para positions.

The microorganisms which are used in the process of this invention are Absidia and certain species of Aspergillus and Cunninghamela; Preferred for use in the process of this invention is Absidia. Illustrative of particularly preferred microorganisms that can be used in the process of this invention are: *Absidia pseudocylindrospora* NRRL 2770; *Absidia ramosa* NRRL 1332; *Absidia glauca* NRRL 1324; Absidia species NRRL 1341; *Aspergillus niger* NRRL 599; *Absidia spinosa* NRRL 1347; *Cunninghamela echinulata* NRRL 1386; *Cunninghamela elegans* 1392; and *Cunninghamela elegans* 1393. *Aspergillus niger* and *Absidia ramosa* are useful for producing the monohydroxy product and the other microrganisms are useful for producing both the dihydroxy and the monohydroxy product.

In a preferred embodiment of the process of this invention, the microorganism is cultivated in a suitable medium prior to contacting with the biphenyl reactants. While not preferred, the microorganism can also be cultivated in the presence of the biphenyl reactant. The medium to be used for the cultivation of the microorganism may be any of the usual ones which are commonly used for the cultivation of microorganisms. A typical medium will include a carbon source, a nitrogen source, inorganic salts and deionized water. Illustrative of suitable carbon sources are aromatic or aliphatic carbon compound, such as n-parafin, glucose, maltose and the like. Suitable nitrogen sources include inorganic nitrogen compounds, organic nitrogen compounds or mixtures thereof. Illustrative of useful inorganic nitrogen compounds are ammonium chloride, ammonium nitrate, ammonium sulfate, ammonium phosphate and the like. Useful organic nitrogen compounds include peptone, neopeptone, soytone, corn, yeast extract liquor, soybean powder and the like. As an optional component the culture medium may also include one or more inorganic salts and one or more trace elements. For the inorganic salt component sodium chloride; potassium phosphate; potassium phosphate; sodium, iron, magnesium, and manganese sulfates may be used. For the trace elements, boric acid; copper and zinc sulfate; copper chloride or the hydrochloride compound of magnesium, iron, manganese, cobalt, zinc or copper and the like may be used.

The pH of the culture medium is not critical and may vary from about 4.0 to about 8.0, and preferably from about 5.6 to about 7.2. The cultivation temperature is not critical and may vary from about 20° to about 40° C.

In carrying out the process of this invention any of the above described microorganisms is grown in a culture medium containing the above described nutrient sources. An appropriate biphenyl compound is then added at any time between the beginning of microorganism growth and the end of microorganism growth. The biphenyl compound can also be added after the microorganism has been concentrated and redeposited into the culture medium. The biphenyl compound may be added neat or dissolved in a suitable solvent such as ethanol, methanol, dimethylformamide and the like. The concentration of the microorganism required to effect the process of this invention is not critical. In the preferred embodiments, microorganism concentration will be at least 0.5 weight percent based on the weight of the reaction mixture. In particularly preferred embodiments, the concentration of the microorganism is at least 1.0 weight percent.

The concentration of the biphenyl reactant is not critical. In the preferred embodiments of the process of this invention, the concentration of biphenyl reactant can vary from about 0.005 to about 10 weight percent, based on the total weight of the reaction mixture.

After the addition of the biphenyl reactant, the process is effected for a period of time sufficient to produce the desired hydroxy biphenyl compound. In general, residence times may vary from about one day to twenty days or longer. It should be appreciated that reaction times are influenced to a significant degree by pH; reaction temperature; the concentration and choice of microorganisms; the concentration and choice of reactant and other factors known to those of skill in the art.

After the process of this invention has gone to completion, the desired product can be collected in pure form by conventional methods. Thus, for example, the mycelium can be removed from the water/product by filtration and the product collected using ion, gas chromotography, extraction, thin layer chromotography, distillation and the like.

The following specific examples are made to more particularly illustrate the process of this invention. The following materials and methods were employed in Examples 1 to 16.

Microorganisms

The following fungi were obtained from Northern Regional Research Laboratories, Agricultural Research Service, U.S.D.A. (Peoria, Illinois); *Absidia pseudocylindrosporo* NRRL 2770; *Absidia ramosa* NRRL 1332; *Absidia glauca* NRRL 1324; Absidia species NRRL 1341, *Absidia spinosa* NRRL 1347; *Aspergillus niger* NRRL 599; *Cunninghamella echinulata* 1386; *Cunninghamella elegans* NRRL 1392; and *Cunninghamella elegans* NRRL 1393. The fungus cultures were maintained on Sabourand Agar slants.

Culture Media

Four types of media were used. Their composition is set forth in Table I, below.

TABLE I

| I. Sabourand Broth (SB): | |
|---|---|
| Component | Amount |
| a. Neopeptone | 10 g |
| b. Glucose | 20 g |
| c. Deionized water | 1 liter |
| pH | 5.7 |
| II. Subourand Agar (SA): | |
| Component | Amount |
| a. Neopeptone | 10 g |
| b. Maltose | 40 g |
| c. Agar | 15 g |
| d. Deionized water | 1 liter |
| pH | 5.6 |

TABLE I-continued

| III. Smith Rosazza Broth (SRB): | |
|---|---|
| Component | Amount |
| a. Soytone | 5 g |
| b. Glucose | 20 g |
| c. Yeast extract | 5 g |
| d. NaCl | 5 g |
| e. $K_2HPO_4$ | 5 g |
| f. Deionized water | 1 liter |
| pH | 7.0 |
| IV. $P_1$ Minimal Medium (PMM): | |
| Component | Amount |
| a) $(NH_4)_2HPO_4$ | 10 g |
| b) $K_2HPO_4$ | 5 g |
| c) $Na_2SO_4$ | .5 g |
| d) $CaCl_2$ (50g/l) | 1 ml |
| e) Solution containing: 1) 40g of $MgSO_4 . 7H_2O$ 2) 2g of $FeSO_4 . 7H_2O$ 3) 1.64g of $Mn_nSO_4 . H_2O$ 4) 2.0g of NaCl 5) 1 liter of deionized $H_2O$ | 1 ml |
| f) Solution containing: 1) .50g of $H_3BO_3$ 2) .04g of $CuSO_4 . 5H_2O$ 3) .20g of $Na_2MoO_4 . H_2O$ 4) 8g of $ZnSO_4 . 7H_2O$ 5) .20g of $CuCl_2 . 6H_2O$ 6) 1 liter of deionized $H_2O$ | 1 ml |
| g deionized $H_2O$ | 1 l |
| h. Agar (optional) | 15 g |
| I Glucose | 2% wt./volume |
| PH.. 7.2 | |

Before inoculation the media were sterilized by autoclaving at 15 lbs for 15 minutes. For PMM media, glucose was sterilized separately and added as the carbon and energy source.

Procedure

Sterilized media was added to sterilized petri dishes. The media are inoculated with microorganisms and were allowed to incubate for 2 to 6 days. Pieces of the mycelium were transferred from the petri dishes to 500 ml baffled shake flasks containing 100 ml of one of the medium described above. For concentrated mycelium studies, following four to six days growth, the mycelium were concentrated on filter paper and resuspended in a 500 ml baffled shake flask containing 100 ml of the same medium in which the microorganism was grown; or the mycelium were concentrated an additional 2 to 4 fold. The shake flask were then incubated on a reciprocal shaker for from about one to about 20 days at a temperature of from about 28° to about 32° C.

One ml of a solution containing 350 grams of biphenyl per one liter of dimethylformamide was added to 100 ml of culture medium no less than eighteen hours after inoculation for growing mycelia and at the time of concentration for concentrated mycelia and incubated for from one to twenty one days. After the completion of the cultivation period, the culture and broth were extracted with ethyl acetate and the ethyl acetate separated by centrifugation. The ethyl acetate was then analyzed for hydroxyated biphenyl content.

The presence of hydroxylated biphenyls was determined by thin layer chromatography (TLC) (qualitative) and gas chromatography (GC) (quantitative) by comparing $R_f$ values and retention times, respectively, of the unknowns to authentic samples. For both procedures five parts fementation broth were extracted with one part ethyl acetate and the phases separated by centrifugation. For the GC assay, prior to extraction, 1-hexadecene was added to the ethyl acetate as an internal standard (36.8 ug 1-hexadecene/ml ethyl acetate).

20×20 CM. Sil-G25 UV$_{254}$ silica gel plates (Brinkman) (Trademark) were used for TLC analysis. Ten ml of the ethylacetate extracts were spotted at the origin, dried, and eluted with chloroform: acetone (80:20 v/v) for 60 min. Product spots were visualized under UV light. A standard mixture was run with each plate. The R$_f$ values of interest are: biphenyl, 0.79; 4-hydroxybiphenyl, 0.51; 4,4'-dihydroxybiphenyl, 0.38. GC analysis was carried out with the trifluoroacetoxy derivatives.

These derivatives of the hydroxylated biphenyls were prepared as follows: To 0.5 ml ethyl acetate extract containing 1-hexadecene (internal standard) is added 5 ul triethylamine followed by the slow addition of 0.5 ml trifluoroacetic anhydride and waiting 2 minutes for the reaction to be completed.

The assay was performed using a Hewlett-Packard Model 5830-A gas chromatograph equipped with a flame ionization detector. Injection port and detector temperatures were 220° and 250° C., respectively. The column was 10 feet by ¼ inch stainless-steel packed with 10% Apiezon L on 60/80 Chromosorb W (acid washed, silinated). An isothemal temperature of 170° C. was maintained, and the carrier gas flow was 37 ml of helium/min. The phenols were quantitated by measuring the ratio of the phenol peak area to the peak area of 1-hexadecene.

The results of the experiments are summarized in TABLES II and III set forth hereinbelow.

TABLE II

BIPHENYL HYDROXYLATION IN SABOURAND BROTH AND SMITH-ROSAZZA BROTH MEDIA

BIPHENYL HYDROXYLATION PRODUCTS, µg/ml

| | | GROWING MYCELIA$^c$ | | | | CONCENTRATED "GROWING" MYCELIA$^d$ | | | |
|---|---|---|---|---|---|---|---|---|---|
| | | 4-Hydroxybiphenyl | | 4,4'-Dihydroxybiphenyl | | 4-Hydroxybiphenyl | | 4,4'-Dihydroxybiphenyl | |
| EXAMPLE | MICROORGANISM | S-RB | SB | S-RB | SB | $^b$S-RB | SB | S-RB | SB |
| I. | $^a$Absidia pseudocylindrospora 2700 | 45.8 | 54.4 | 57.0 | 23.6 | 38.8 | 13.8 | 24.1 | 30.8 |
| II. | $^a$Absidia ramosa 1332 | 0 | 0 | 0 | 0 | 10.4 | 0 | 0 | 0 |
| III. | $^a$Absidia glauca 1324 | 17.8 | ND$^b$ | 13.5 | ND$^b$ | 17.1 | ND$^b$ | 10.3 | ND$^b$ |
| IV. | Absidia sp. 1341 | 37.8 | ND$^b$ | 61.6 | ND$^b$ | 63.9 | ND$^b$ | 75.6 | ND$^b$ |
| V. | Absidia spinosa 1347 | 15.5 | ND$^b$ | 0 | ND$^b$ | 5.9 | ND$^b$ | 9.5 | ND$^b$ |
| VI. | $^a$Cunninghamela echinulata 1386 | 20.3 | 37.5 | 3.9 | 0 | 19.2 | 12.0 | 1.0 | 1.8 |
| VII. | $^a$Cunninghamela elegans 1392 | 5.8 | 2.6 | 0 | 0 | 7.8 | 7.8 | 1.1 | 0 |
| VIII. | $^a$Cunninghamela elegans 1393 | 0 | 0 | 0 | 0 | 11.6 | ND$^b$ | 0 | ND$^b$ |
| IX. | Aspergillus niger 599 | 2.7 | ND$^b$ | 0 | ND$^b$ | 0 | ND$^b$ | 0 | ND$^b$ |

$^a$Examined during 18 day incubation (growing Mycelia) or 14 day incubation (Conc. Mycelia in presence of biphenyl. The other strains incubated for 10 days (growing Mycelia) and 7 days (Conc. Mycelia) in presence of biphenyl.
$^b$Not determined
$^c$biphenyl added 17 hours after inoculation
$^d$biphenyl added at the time of Mycelia concentration

TABLE III

BIPHENYL HYDROXYLATION IN P MINIMAL MEDIUM

A. Biphenyl Added Two Days After Inoculation

BIPHENYL HYDROXYLATION PRODUCTS (µg/ml)

| | | 3 Days | | 6 Days | | 11 Days | |
|---|---|---|---|---|---|---|---|
| EXAMPLE | MICROORGANISM | 4-OH* | 4,4'-diOH** | 4-OH* | 4,4'-diOH** | 4-OH* | 4,4'-diOH** |
| IX | Absidia psuedocylindrospora 2770 | 6.0 | 4.1 | 6.7 | 4.9 | 23.1 | 10.2 |
| X | Absidia ramosa 1332 | 0 | 0 | 0 | 0 | 0 | 0 |
| XI | Cunninghamela echinulata 1386 | 6.6 | 0 | 10.0 | 0 | 9.7 | 0 |
| XII | Cunninghamela elegans 1392 | 8.3 | 0 | 6.6 | 0 | 16.6 | 0 |
| XIII | Cunninghamela elegans 1393 | 0 | 0 | 0 | 0 | 0 | 0 |

B. BIPHENYL Added At The Time of Inoculation

BIPHENYL HYDROXYLATION PRODUCTS (µg/ml)

| | | 1 Day | | 3 Days | | 6 Days | | 9 Days | | 13 Days | |
|---|---|---|---|---|---|---|---|---|---|---|---|
| EXAMPLE | MICROORGANISM | 4-OH* | 4,4'-diOH** | 4-OH* | 4,4'-diOH** | 4-OH* | 4,4'-diOH** | 4-OH* | 4,4'-diOH** | 4-OH* | 4,4'-diOH** |
| XIV | Absidia pseudocylindrospora 2770 | 2.5 | 0 | 6.0 | 3 | 0.5 | 5 | 6.5 | 2.0 | 6.5 | 2.0 |
| XV | Absidia species 1341 | 2.0 | 0 | 9.0 | 7.0 | 12.0 | 8.0 | 7.0 | 7.0 | 7.0 | 5.0 |

*4-OH is 4-hydroxybiphenyl
**4,4'-diOH is 4,4'-dihydroxybiphenyl

The biphenyl compounds prepared in accordance with the process of this invention have wide utility and are valuable for a number of useful purposes. For example, monomer, 4,4'-dihydroxybiphenyl is extremely useful as a precursor in the preparation of polymer of high strength and heat resistance. Other of these compounds are useful as heat transfer agents or as precursors in the preparation of photocurable resins. It should be pointed out, however, that other hydroxylated biphenyl compounds prepared by the process of this invention are not limited to use as described above but in addition are extremely useful for other purposes which are known to those skilled in the art.

Various modifications and variations of this invention will be obvious to a worker skilled in the art and it is to be understood that such modifications are to be included within the purview of this application and the spirit and scope of the appended claims.

What is claimed is:

1. A microbiological transformation process for preparing a hydroxylated compound of the formula:

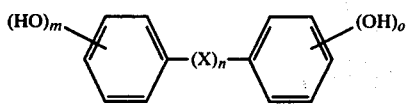

by contacting a compound of the formula:

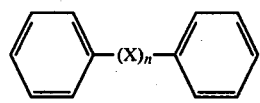

with a microorganism selected from the genus Absidia, for a period of time sufficient to produce any amount of said hydroxylated compound, wherein
- m, n and o are individually 0 or 1, with the proviso that both m, n and o are individually 0 or 1, with the proviso that both n and o cannot be 0;
- X is one or more divalent phenyl, oxygen, sulfur, sulfinyl, sulfonyl, carbonyl, amino or alkylamino; or X is a divalent alkylene, alkenylene, alkynylene, cycloalkylene or cycloalkenylene chain which may optionally include one or more divalent oxygen, sulfur, sulfinyl, sulfonyl, carbonyl, amino or alkylamino moieties in any combination.

2. A process according to claim 1 which is carried out by growing cells of said microorganisms cultured in a medium at a pH value of from about 4.0 to about 8.0 and containing assimilable carbon sources, nitrogen sources and other nutrients necessary for the growth of the microorganism at a temperature of from about 20° to about 40° C.

3. A process according to claim 1 which is carried out by concentrated biomass of said microorganism cultured in a medium at a pH value of from about 4.0 to about 8.0 and containing assimilable carbon sources, nitrogen sources and other nutrients necessary for the growth of the microorganism at a temperature of from about 20° to about 40° C.

4. A process according to claim 1 wherein said microorganism is *Absidia psuedocylindiospora* NRRL 2770.

5. A process according to claim 1 wherein said microorganism is *Absidia ramosa* NRRL 1332.

6. A process according to claim 1 wherein said microorganism is *Absidia glauca* NRRL 1324.

7. A process according to claim 1 wherein said microorganism is Absidia sp. NRRL 1341.

8. A process according to claim 1 wherein said microorganism is *Absidia spinosa* NRRL 1347.

9. A process according to claim 1 wherein m and o are 1 and the hydroxyl groups are substituted in the para positions.

10. A process according to claim 1 wherein x is divalent alkylene, alkenylene, alkynylene, phenyl, oxygen, sulfur, sulfinyl or sulfonyl.

11. A process according to claim 1 wherein n is 0.

12. A process according to claim 1 wherein said microorganism is selected from the group consisting of *Absidia pseudocylindrospora* NRRL 2770; *Absidia ramosa* NRRL 1332; *Absidia glauca* NRRL 1324; Absidia sp. NRRL 1341 and *Absidia spinosa* NRRL 1347.

13. A process according to claim 1 wherein:
- m and o are 1 and the hydroxyl groups are substituted at the para positions;
- X is divalent alkylene, alkenylene, alkynylene, phenylene, oxygen, sulfur, sulfinyl or sulfonyl.

* * * * *